United States Patent [19]

Umio et al.

[11] 4,001,280
[45] Jan. 4, 1977

[54] CHROMONE DERIVATIVES

[75] Inventors: Suminori Umio, Kawanishi; Ikuo Ueda, Yao; Masaaki Matsuo, Toyonaka; Masakazu Kobayashi, Ikeda; Osamu Nakaguti, Osaka; Yoshinari Sato, Tanashi, all of Japan

[73] Assignee: Fujisawa Pharmaceutical Co., Ltd., Osaka, Japan

[22] Filed: June 20, 1973

[21] Appl. No.: 371,852

[30] Foreign Application Priority Data

June 21, 1972 Japan .............................. 47-62626
June 24, 1972 Japan .............................. 47-63407
June 29, 1972 Japan .............................. 47-65573

[52] U.S. Cl. ................... 260/340.5; 260/268 TR; 260/268 BC; 260/302 A; 260/302 D; 260/302 H; 260/304 R; 260/304 A; 260/304 D; 260/340.3; 260/345.2; 424/251; 424/270; 424/282; 424/283

[51] Int. Cl.² .................................. C07D 311/24
[58] Field of Search .......... 260/340.5, 340.3, 345.2

[56] References Cited

UNITED STATES PATENTS

| | | | |
|---|---|---|---|
| 3,427,324 | 2/1969 | Fitzmaurice | 260/340.7 |
| 3,484,445 | 12/1969 | Lee et al. | 260/294 |
| 3,629,290 | 12/1971 | Cairns et al. | 260/345.2 |
| 3,786,071 | 1/1974 | Cairns et al. | 260/345.2 |
| 3,882,148 | 5/1975 | Augstein | 260/345.2 |

FOREIGN PATENTS OR APPLICATIONS 2,237,100  7/1972  Germany

OTHER PUBLICATIONS

Allinger et al., *Organic Chemistry*, (1972), p. 247.

*Primary Examiner*—Anton H. Sutto
*Assistant Examiner*—Michael Shippen
*Attorney, Agent, or Firm*—Bierman & Bierman

[57] ABSTRACT

Chromone derivatives of the formula:

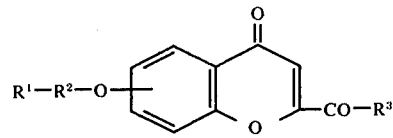

wherein $R^1$ is alkoxy, an N,S-containing heterocyclic group or aryloxy in which heterocyclic group may be substituted with halogen or acyl, and aryl may be substituted with amino, alkylamino, acylamino, nitro or alkylenedioxy; $R^2$ is alkylene; $R^3$ is hydroxy, alkoxy or a group of the formula

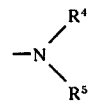

in which $R^4$ is hydrogen, $R^5$ is hydroxy or amino or $R^4$ and $R^5$ means taken together with the adjacent nitrogen atom, piperazinyl substituted with alkyl or hydroxyalkyl; provided that when $R^3$ is hydroxy or alkoxy, $R^1$ is an N,S-containing heterocyclic group or aryloxy in which heterocyclic group is substituted with halogen or acyl, and aryl is substituted with amino, alkylamino, acylamino, nitro or alkylenedioxy, and nontoxic, pharmaceutically acceptable salt thereof. These compounds are useful as anti-allergic agents.

4 Claims, No Drawings

CHROMONE DERIVATIVES

This invention relates to new chromone derivatives which possess an anti-allergic activity, a process for preparing the same and a composition thereof.

The chromone derivatives can be represented by the following general formula:

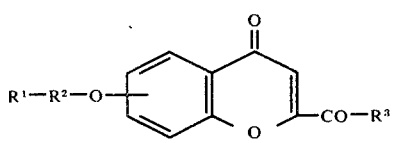

[I]

wherein $R^1$ is alkoxy, an N,S-containing heterocyclic group or aryloxy in which heterocyclic group may be substituted with halogen or acyl, and aryl may be substituted with amino, alkylamino, acylamino, nitro or alkylenedioxy; $R^2$ is alkylene; $R^3$ is hydroxy, alkoxy or a group of the formula

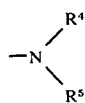

in which $R^4$ is hydrogen, $R^5$ is hydroxy or amino or $R^4$ and $R^5$ means taken together with the adjacent nitrogen atom piperazinyl substituted with alkyl or hydroxyalkyl; provided that when $R^3$ is hydroxy or alkoxy, $R^1$ is an N,S-containing heterocyclic group or aryloxy in which heterocyclic group is substituted with halogen or acyl, and aryl is substituted with amino, alkylamino, acylamino, nitro or alkylenedioxy.

It has been found that the chromone derivatives of the formula [I] possess an anti-allergic activity, and may be useful in a therapeutic and precautionary treatment for asthma.

The object of the present invention is to provide new chromone derivatives of the formula [I]. There are accordingly provided the new chromone derivatives of the formula [I] possessing an anti-allergic activity and being useful in a therapeutic and precautionary treatment for asthma. Furthermore, there may be provided a pharmaceutical composition comprising, as an active ingredient, the new chromone derivatives of the formula [I] and pharmaceutically acceptable carriers, useful as therapeutic and precautionary agents for asthma.

According to a still further feature of the invention, there are provided a process for preparing the new chromone derivatives of the formula [I]. Other objects and advantageous features of the invention will be apparent to those conversant with the art to which the present invention pertains from the subsequent descriptions.

The process included in the invention is mentioned in the following scheme:

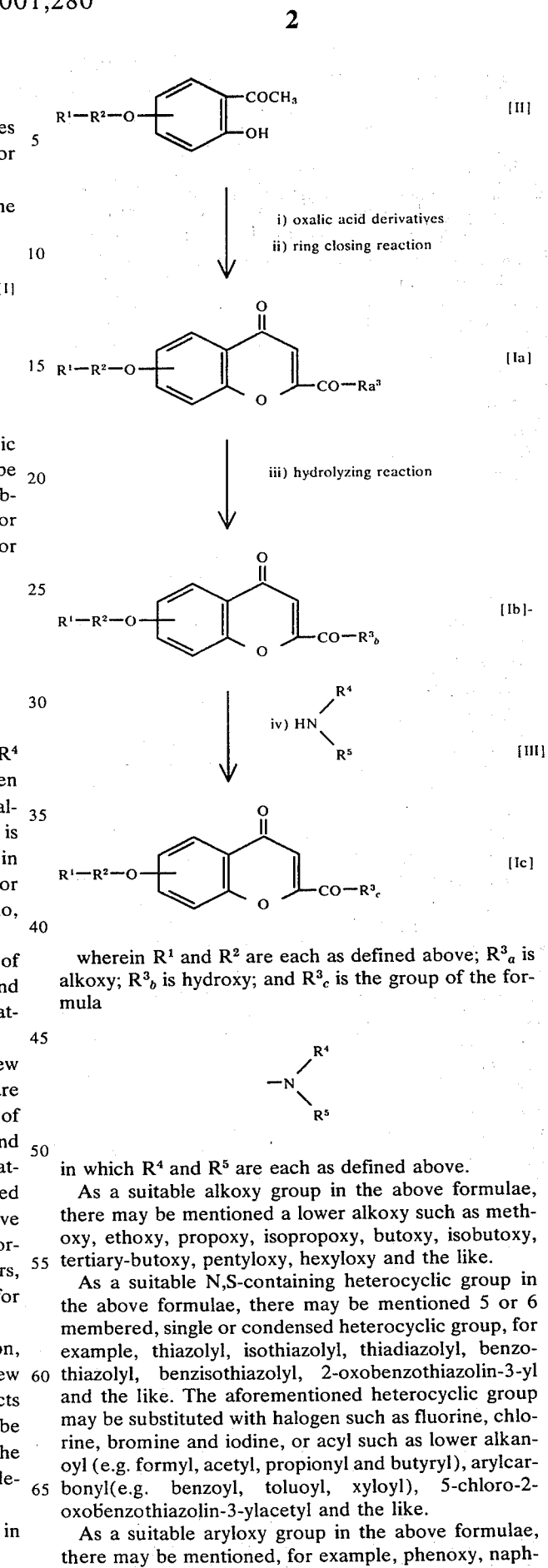

wherein $R^1$ and $R^2$ are each as defined above; $R^3_a$ is alkoxy; $R^3_b$ is hydroxy; and $R^3_c$ is the group of the formula $$-N\begin{matrix}R^4\\R^5\end{matrix}$$

in which $R^4$ and $R^5$ are each as defined above.

As a suitable alkoxy group in the above formulae, there may be mentioned a lower alkoxy such as methoxy, ethoxy, propoxy, isopropoxy, butoxy, isobutoxy, tertiary-butoxy, pentyloxy, hexyloxy and the like.

As a suitable N,S-containing heterocyclic group in the above formulae, there may be mentioned 5 or 6 membered, single or condensed heterocyclic group, for example, thiazolyl, isothiazolyl, thiadiazolyl, benzothiazolyl, benzisothiazolyl, 2-oxobenzothiazolin-3-yl and the like. The aforementioned heterocyclic group may be substituted with halogen such as fluorine, chlorine, bromine and iodine, or acyl such as lower alkanoyl (e.g. formyl, acetyl, propionyl and butyryl), arylcarbonyl(e.g. benzoyl, toluoyl, xyloyl), 5-chloro-2-oxobenzothiazolin-3-ylacetyl and the like.

As a suitable aryloxy group in the above formulae, there may be mentioned, for example, phenoxy, naphthyloxy, tolyloxy, xylyloxy, mestyloxy, cumenyloxy and the like. The aforementioned aryloxy group may be substituted with amino, alkylamino such as lower one (e.g. methylamino, ethylamino, propylamino, butylamino, dimethylamino, diethylamino and dipropylamino), acylamino such as lower alkanoylamino (e.g. formamido, acetamido, propionamido and butyramido), and arylcarbonylamino (e.g. benzamido), nitro or alkylenedioxy such as lower one (e.g. methylenedioxy, ethylenedioxy, propylenedioxy).

As a suitable alkylene group in the above formulae, there may be mentioned lower alkylene group such as methylene, ethylene, trimethylene, tetramethylene, pentamethylene, hexamethylene, propylene, 2-methyltrimethylene and the like.

As a suitable group of the formula

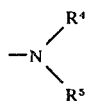

in the above formulae, there may be mentioned a hydroxyamino group, hydrazino group or 1-piperazinyl group. The aforementioned 1-piperazinyl group is substituted at the 4-position with alkyl such as lower one (e.g. methyl, ethyl, propyl, isopropyl, butyl, isobutyl, tirtiary-butyl, pentyl and hexyl) or hydroxyalkyl such as hydroxy (lower) alkyl (e.g. hydroxymethyl, 2-hydroxyethyl, 2-hydroxypropyl, 3-hydroxypropyl, 4-hydroxybutyl, 5-hydroxypentyl and 6-hydroxyhexyl).

In this specification, the term lower is intended to mean the straight or branched carbon chain having 1 to 6 carbon atoms.

The compound of the formula [Ia] can be prepared by reacting a compound of the formula [II] with an oxalic acid derivative and then reacting the resulting compound with an acid. The reaction may be carried out usually in a solvent inert to the reaction.

As a suitable oxalic acid derivative, there may be mentioned, for example, dialkyl oxalate (e.g. diethyl oxalate), alkyl 2-alkoxy-2,2-dihalogenoacetate (e.g. ethyl 2-ethoxy-2,2-dichloroacetate), alkyloxalylhalide (e.g. ethyloxalylchloride), alkyl glyoxalate (e.g. ethyl glyoxalate) and the like, the alkyl moieties appearing wherein are preferable wherein are preferable to be lower ones.

As a suitable solvent in the reaction, there may be mentioned, for example, ether, dioxane, ethanol, benzene and the like. The reaction is usually carried out under heating, though the reaction temperature is not particularly restricted.

When dialkyl oxalate is used as an oxalic acid derivative, the reaction is preferably carried out in the presence of a basic catalyst such as alkali metal (e.g., lithium, sodium, potassium, etc.), metal alkoxide (e.g., lithium methoxide, lithium ethoxide, sodium methoxide, sodium ethoxide, sodium propoxide, sodium isopropoxide, potassium methoxide, potassium ethoxide, calcium methoxide, magnesium methoxide, aluminium methoxide, etc.), alkali metal amide (e.g., lithium amide, sodium amide, potassium amide, etc.), alkali metal hydride (e.g., lithium hydride, sodium hydride, potassium hydride, etc.), Grignard reagent (e.g., ethyl magnesium bromide, isopropyl magnesium bromide, diethylamino magnesium bromide, diisopropylaminomagnesium bromide, mesityl magnesium bromide, etc.), trityl alkali metal (e.g., trityllithium, tritylsodium, tritylpotassium, etc.), and the like.

When alkyl 2-alkoxy-2,2-dihalogenoacetate is used as an oxalic acid derivative, the reaction is preferably carried out in the presence of a metal catalyst such as platinum, palladium, ruthenium and the like.

When alkyloxalyhalide is used as an oxalic acid derivative, the reaction is preferably carried out in the presence of an acid such as hydrochloric acid.

The ring closing reaction of the resulting reaction product is carried out by reacting it with an acid, for example, hydroiodic acid, hydrochloric acid, hydrobromic acid, acetic acid, sulfuric acid and the like. The reaction can be carried out using two or more kinds of said acids at the same time and/or using a solvent such as alcohol (e.g., methanol, ethanol, etc.), and the like. The reaction temperature is not particularly restricted, but the reaction is usually carried out under warming or heating.

The compound of the formula [Ib] can be prepared by hydrolyzing the resulting compound [Ia].

The hydrolyzing reaction is carried out by an usual method, for instance, by warming or heating the aqueous solution of the compound [Ia], preferably in the presence of a basic catalyst as same as one applied for the reaction of the compound [II] with dialkyl oxalate; an acidic catalyst such as hydrochloric acid, formic acid and acetic acid; or a basic or an acidic ion-exchange resin.

The compound of formula [Ic] can be prepared by reacting the compound of the formula [Ib] or its reactive derivative with the compound of the formula [III] in a solvent inert to the reaction.

As a suitable reactive derivative of the compound [Ib], there may be mentioned, for example, an acid azide, an acid halide such as acid bromide, acid chloride, an mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid), aromatic carboxylic acid (e.g. benzoic acid), or symmetrical acid anhydride, an acid amide with imidazole, 4-substituted imidazole, dimethylpyrazole, triazole or tetrazole, an activated acid ester such as cyanomethyl ester, methoxymethyl ester, vinyl ester, propargyl ester, p-nitropenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide or N-hydroxyphthalimide.

In this reaction, a condensing agent may be added. The suitable examples of the condensing agent may be N,N'-dicyclohexylcarbobiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimdazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sulfophenyl)isoxazolium hydroxide intermolecular salt, (chloromethylene)dimethylammonium chloride, and the like.

As a suitable solvent, there may be mentioned, for example, benzene, ether, methanol, acetone, dioxane, acetonitrile, chloroform, methylenechloride, tetrahydrofuran, ethyl acetate, pyridine and the like. The reaction temperature is not particularly restricted and the reaction is usually carried out under coating or at room temperature.

The compound of the formula [III] may be used in an acid salt form, such as hydrochloric acid salt, acetic acid salt and the like. The reaction may be carried out in the presence of a basic substance such as alkalimetal bicarbonate (e.g. potassium bicarbonate, sodium bicarbonate), trialkylamine (e.g. trimethylamine, triethylamine), pyridine and the like.

The compound of the formula [Ib] and [Ic] may be converted to a nontoxic, pharmaceutically acceptable salt.

As a suitable salt for the compound of the formula [IB], there may be mentioned, for example, an alkaline metal salt such as sodium salt, potassium salt and the like. And as a suitable salt for the compound of the formula [Ic], there may be mentioned, for example, an inorganic acid salt such as hydrochloric acid salt or an organic acid salt such as acetic acid salt, maleic acid salt and the like.

The chromone derivatives of the formula [Ia] [Ib] and [Ic] exhibit an anti-allergic activity and can be used as a drug for treatment of asthma. The test results on some representative compounds of this invention are shown below.

TEST METHOD

Five male Sprague-Dawley JCL strain rates weighing 290–310g. were used for each dose. The animals were sensitized by intracutaneous injection of 0.1ml. of 5 times diluted reagin-like rat antiserum at 48 hours before egg albumin at their depilated backs and were injected 0.1ml. of 4 times diluted hyperimmune rat antiserum at 4 hours before. One ml. of mixture of egg albumin 5 mg. and Evans blue 5 mg. was injected intravenously. Immediately before 0.1ml. of 0.2% histamine solution was injected intracutaneously.

One hour after the injection of the antigen and dye, animals were sacrificed and the skin of the back was removed. The dye of blue spot was then extracted from the skin. The blue spot areas of the skin were punched out and were cut with clipper into small pieces. The small pieces per one blue spot were blended with 10 ml. of a 4:1 mixture of acetone and 2% solution of RBS-25 (Marumoto industrial Co., Ltd.) and rested for 16 hours. Five and 16 hours after, it was shaked for 30 minutes respectively. After centrifugation at 2000 rpm for 15 minutes, the optical density of the supernatant was determined at 620 m$\mu$.

The drug was given orally 2 hours before antigen or intravenously 30 seconds before. The mean amount of dye of the test animals was compared with that of the control animals. The percent inhibition for each dose was calculated.

TEST RESULT

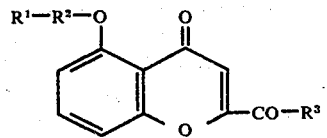

| COMPOUND | | | | | | | |
|---|---|---|---|---|---|---|---|
| $R^1$ | $R^2$ | $R^3$ | A | B | C | D | E |
| $\begin{array}{c}H_3C\\ \phantom{H_3}\diagdown\\ \phantom{H_3C}CH-O-\\ \phantom{H_3}\diagup\\ H_3C\end{array}$ | $-CH_2CH_2-$ | $-N\underset{\phantom{x}}{\diagup\diagdown}N-CH_3$ | p.o. | 60 min. | 125<br>250<br>500 | | 53.9<br>58.3<br>47.0 |
| | | | i.p. | 30 min. | 4<br>16<br>64<br>125 | | 4.0<br>22.3<br>72.9<br>48.2 |
| $\bigcirc\!\!-\!O-$ | " | " | | 30 min. | 250<br>500<br>125 | | 66.7<br>90.6<br>49.9 |
| | | | p.o. | 60 min. | 250<br>500<br>125 | | 45.8<br>46.5<br>37.6 |
| | | | | 120 min. | 250<br>500 | | 40.6<br>67.7 |
| $\begin{array}{c}H_3C\\ \phantom{H_3}\diagdown\\ \phantom{H_3C}N\!-\!\!\bigcirc\!-\!O-\\ \phantom{H_3}\diagup\\ H_3C\end{array}$ | " | $-OH$<br>(Na salt) | i.v. | 30 sec. | 2<br>8<br>32 | 49<br>78.2<br>67.7 | 39.7<br>79.6<br>73.2 |
| $\begin{array}{c}\phantom{xx}O\\ \diagup\diagdown\\ O\!-\!\!\bigcirc\!-\!O-\end{array}$ | " | "<br>(Na salt) | " | " | 2<br>8<br>32 | 50.7<br>72.1<br>80.0 | 4.3<br>72.4<br>60.6 |

-continued

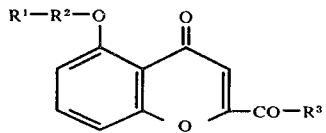

| COMPOUND | | | | | | | |
|---|---|---|---|---|---|---|---|
| R¹ | R² | R³ | A | B | C | D | E |
| Cl-[benzothiazolinone]=O | " | " (Na salt) | " | " | 2<br>8<br>32 | 22.8<br>27.7<br>63.6 | 28.1<br>71.3 | in the above table
"A" means administration route
"B" means pretreatment time
"C" means dose (mg./kg.)
"D" means inhibition % for Reagin-like antiserum
"E" means inhibition % for Hyperimmune antiserum Thus, the chromone derivatives of the formulae [Ia], [Ib] and [Ic] are useful as an anti-allergic drug.

They can be administered by the conventional methods, the conventional types of unit dosages or with the conventional pharmaceutical carriers to produce an anti-allergic activity in human beings. Thus, they can be used in the form of pharmaceutical preparations, which contain them in admixture with a pharmaceutical organic or inorganic carrier material suitable for enteral or parenteral applications. Oral administration by the use of tablets, capsules or in liquid form such as suspensions, solutions or emulsions, or injectional application is particularly advantageous. When formed into tablets, the conventional binding and disintegrating agents used in therapeutic unit dosages can be employed. Illustrative of binding agents there can be mentioned glucose, lactose, gum acacia, gelatin, mannitol, starch paste, magnesium trisilicate and talc. Illustrative of disintegrating agents there can be mentioned corn starch, keratin, colloidal silica and potato starch. When administered as liquids the conventional liquid carriers can be used.

The dosage or therapeutically effective quantity of the chromone derivatives of the formulae [Ia], [Ib] or [Ic] for human beings can very over wide limits such as that of about 10 to 1000 milligrams/day for adult. The upper limit is limited only by the degree of effect desired and economic considerations. For oral administration it is to employ from about 1 to 30 milligrams of the therapeutic agent per unit dosage. For injectional use, the active ingredient may be employed from 1 to 10 mg per unit dosage. Of course, the dosage of the active ingredient agent used can vary considerably, such as the age of the patient and the degree of therapeutic effect desired. By the term pharmaceutical carrier it is intended to include non-therapeutic materials which are conventionally used with unit dosage and includes fillers, diluents, binders, lubricants, disintegrating agents and solvents. Of course, it is possible to administer the active ingredient, i.e. the pure compound, without the use of a pharmaceutical carrier.

Also, it is desirable to administer the active ingredient with a mixture of the other therapeutics such as bronchodilator.

EXAMPLE 1

(1) Ethyl 5-[2-(2-oxo-5-chlorobenzotiazolin-3-yl)ethoxy] chromone-2-carboxylate.

2-[2-(2-oxo-5-chlorobenzothiazolin-3-yl)ethoxy]-6-hydroxyacetophenone (3.08g.) and diethyl oxalate (2.05g.) were dissolved in benzene. The resultant solution was added dropwise at room temperature to the suspension of sodium ethoxide obtained from sodium metal (0.25g.) and absolute ethanol in absolute benzene. The mixture was refluxed for an hour. Concentrated hydrochloric acid (20ml.) was added to the mixture under cooling, and then the mixture was stirred for 30 minutes at 80° C. The reaction mixture was extracted with ethyl acetate, and the extract was washed with water, saturated an aqueous solution of sodium bicarbonate and water in order, and dried. The solvent was distilled off under reduced pressure. The residue was recrystallized from a mixture of methanol and ethyl acetate to give colorless crystals (1.4g.) of ethyl 5-[2-(2-oxo-5-chlorobenzothiazolin-3-yl)ethoxy]chromone-2-carboxylate. m.p. 177° – 178.5° C.

(2) Sodium 5-[2-(2-oxo-5-chlorobenzothiazolin-3-yl)ethoxy] chromone-2-carboxylate Ethyl 5-[2-(2-oxo-5-chlorobenzothiazolin-3-yl)ethoxy] chromone-2-carboxylate (1.3g.) was dissolved in 95% ethanol (80ml.). To the solution was added an aqueous solution (5ml.) of sodium carbonate (0.16 g.), and the mixture was refluxed for 40 minutes while nitrogen gas was bubbled. The ethanol was distilled off under reduced pressure, and the residue was recrystallized from aqueous ethanol to give colorless crystals (0.3g.) of sodium 5-[2-(2-oxo-5-chlorobenzothiazolin-3-yl) ethoxy]chromone-2,6carboxylate.
m.p. 190° C (dec.).

Analysis for $C_{19}H_{11}NO_6SClNa \cdot 3\frac{1}{2}H_2O$: Calculated: C 45.42, H 3.61, Na 4.58; Found: C 45.36, H 3.50, Na 4.73

EXAMPLE 2

(1) Ethyl 5-[2-(3,4-methylenedioxyphenoxy)ethoxy]chromone-2-carboxylate

Sodium ethoxide obtained from sodium metal (4.3g.) and absolute ethanol was suspended in absolute benzene. To the suspension was added dropwise a suspension of 2-[2-(3,4-methylenedioxyphenoxy)ethoxy]-6-hydroxyacetophenone (23.5g.) and diethyl oxalate (16.4g.) in absolute benzene. The mixture was refluxed under heating for an hour, acidified with concentrated hydrochloric acid under cooling, and then refluxed under heating for 40 minutes. After cooling, ethyl acetate was added to the reaction mixture, and then the insoluble solid was collected by filtration. The ethyl acetate layer was separated from the filtrate, and concentrated under reduced pressure. The residue was added to a mixture of methanol (10 parts) and hydrochloric acid (1 part), and the mixture was refluxed under heating for 30 minutes. The resultant precipitate collected by filtration and the solid obtained before were combined together and recrystallized from benzene to give colorless needles (15.9g.) of ethyl 5-[2-(3,4-methylenedioxyphenoxy)ethoxy]chromone-2-carboxylate.
m.p. 161° – 162° C.

Analysis for $C_{21}H_{18}O_8$: Calculated: C 63.31, H 4.55; Found: C 63.54, H 4.58

(2) Sodium 5-[2-(3,4-methylenedioxyphenoxy)ethoxy]chromone-2-carboxylate

Ethyl 5-[2-(3,4-methlenedioxyphenoxy)ethoxy]chromone-2-carboxylate (3.98g.) was dissolved in a mixture of acetone (50ml.) and absolute ethanol (200ml.) under heating. To the solution was added an aqueous solution of sodium carbonate (0.55g.) under heating. After the mixture was refluxed under heating for 2 hours, the solvent was distilled off under reduced pressure. The residue was dissolved in water under heating and the insoluble material was filtered off. The filtrate was treated with activated charcoal. Ethanol was added thereto and the resultant solution was allowed to stand. The precipitate was collected by filtration to give crystals (2.5g.) of sodium 5-[2-(3,4-methylenedioxyphenoxy)ethoxy]chromone-2-carboxylate.
m.p. 206° – 208° C (dec.).

Analysis for $C_{19}H_{13}O_8Na \cdot \frac{2}{3}H_2O$: Calculated: C 56.58, H 3.58, Na 5.70; Found: C 56.48, H 3.58, Na 5.95

EXAMPLE 3

(1) Ethyl 5-[2-(3-dimethylaminophenoxy)ethoxy]chromone-2-carboxylate

Sodium ethoxide obtained from sodium metal (0.57g.) and absolute ethanol was suspended in absolute benzene (30ml.). To the suspension was gradually added a solution of 2-[2-(3-dimethylaminophenoxy)ethoxy]-6-hydroxyacetophenone (2.6g.) and diethyl oxalate (3.4g.) in absolute benzene (30ml.). The mixture was refluxed at 80° C for an hour. After cooling to room temperature, the solvent was distilled off with keeping the temperature below 40° C. to give reddish brown pasty residue of sodium 2-ethoxalyacethyl-3-[2-(3-dimethylaminophenoxy)ethoxy]phenolate. The residue was dissolved in absolute ethanol (20ml.), and acidified with concentrated hydrochloric acid under cooling. The resultant solution was refluxed under heating for 1.5 hours. After cooling, water and ethyl acetate were added to the reaction mixture. The aqueous layer was separated from the reaction mixture, and alkalized with 10% aqueous solution of sodium carbonate, and then extracted with ethyl acetate. The extract was washed with water, and dried over magnesium sulfate, and then the solvent was distilled off under reduced pressure. The crude crystals (2.21g.) were purified by column chromatography on silica gel to give ethyl 5-[2-(3-dimethylaminophenoxy)ethoxy]chromone-2-carboxylate (1.65g.). The product was recrystallized from methanol to give colorless needles. m.p. 110.5° – 112.0° C.

Analysis for $C_{20}H_{23}NO_6$: Calculated: C 66.49, H 5.83, N 3.52; Found: C 66.20, H 5.76, N 3.55

(2) Sodium 5-[2-(3-dimethylaminophenoxy)ethoxy]chromone-2-carboxylate

Ethyl 5-[2-(3-dimethylaminophenoxy)ethoxy]chromone-2-carboxylate (2.8g.) was suspended in 99% ethanol (30ml.). To the suspension was added an aqueous solution (10ml.) of sodium carbonate (0.36g.), and the mixture was refluxed under heating for 2 hours in nitrogen atmosphere. The reaction mixture was allowed to stand overnight. The precipitate was collected by filtration, and then recrystallized from 99% ethanol to give pink crystals (2.0g.) of sodium 5-[2-(3-dimethalaminophenoxy) ethoxy]chromone-2-carboxylate.
m.p. 257° – 259° C (dec.).

Analysis for $C_{20}H_{18}NO_6Na \cdot 5/4H_2O$: Calculated: C 58.01, H 4.85, N 3.38; Found: C 58.02, H 4.89, N 3.49

EXAMPLE 4

Ethyl 5-[2-(4-nitrophenoxy)ethoxy]chromone-2-carboxylate

To a suspension of sodium ethoxide obtained from sodium metal (1.82g.) and absolute ethanol in absolute benzene, was added dropwise a suspension of 2-[2-(4-nitrophenoxy)ethoxy]-6-hydroxyacetophenone (10.0g.) and diethyl oxalate (6.9g.) in absolute benzene with stirring at room temperature for an hour. The resultant mixture was refluxed under heating for 2 hours, and then acidified with concentrated hydrochloric acid under cooling. The mixture was refluxed under heating for 30 minutes, and water was added thereto. The reaction mixture was extracted with ethyl acetate, and the extract was washed with water and dried, and then the solvent was distilled off under reduced pressure. The residue was recrystallized from a mixture of ethanol and ethyl acetate to give yellow granules (9.0g.) of ethyl 5-[2-(4-nitrophenoxy)ethoxy]chromone-2-carboxylate. m.p. 158° – 161° C.

EXAMPLE 5

Ethyl 5-[2-(4-acetamidophenoxy)ethoxy]chromone-2-carboxylate

2-[2-(4-acetamidophenoxy)ethoxy]-6-hydroxyacetophenone (3.3g.) was suspended in diethyl oxalate (25ml.). To the suspension was slowly added sodium hydride (2.4g.) with stirring at room temperature. The resultant mixture was stirred at 50° – 60° C for 2 hours, and allowed to stand at room temperature. Benzene (80ml.) and concentrated hydrochloric acid (5ml.) were added to the mixture, and then the mixture was stirred at 50° – 60° C for 30 minutes. The reaction mixture was extracted with ethyl acetate and the extract was washed with 5% aqueous solution of sodium hydroxide and with water and then dried over magnesium sulfate. The solvent was evaporated under reduced pressure, and the residue was recrystallized from a mixture of ethyl acetate and chloroform to give colorless crystals (1.3g.) of ethyl 5-[2-(4-acetamidophenoxy)ethoxy]chromone-2-carboxylate.
m.p. 220° – 222° C.

Analysis for $C_{22}H_{21}NO_7$: Calculated: C 64.23; H 5.15, N 3.41; Found: C 64.34, H 5.03, N 3.50

EXAMPLE 6

Sodium 5-[2-(4-aminophenoxy)ethoxy]chromone-2-carboxylate

A solution of ethyl 5-[2-(4-aminophenoxy)ethoxy]-chromone-2-carboxylate (3.4g.) in 95% ethanol (250ml.) was boiled, to which was added at once an aqueous solution (20ml.) of sodium carbonate (0.5g.) under heating. The resultant mixture was refluxed for 2 hours. After cooling, the ethanol was evaporated under reduced pressure. The residue was recrystallized from 80% aqueous ethanol to give brown scaly crystals (3.5g.) of sodium 5-[2-(4-aminophenoxy)ethoxy]chromone-2-carboxylate.
m.p. 195° – 197° C.

Analysis for $C_{18}H_{14}NO_6Na \cdot H_2O$: Calculated: C 56.70, H 4.23, N 3.67; Found: C 56.59, H 3.93, N 3.58

EXAMPLE 7

Sodium 5-[2-[4-(2-oxo-5-chlorobenzothiazolin-3-ylacetyl)-1-piperazinyl]ethoxy]chromone-2-carboxylate.

Ethyl 5[2[4-(2-oxo-5-chlorobenzothiazolin-3-ylacetyl-1-piperazinyl]ethoxy]chromone-2-carboxylate (4.3g.) was suspended in 99% ethanol (50ml.). To suspension was added an aqueous solution (12ml.) of anhydrous sodium carbonate (0.18g.) and the mixture was refluxed under heating for 3 hours. The reaction mixture was cooled to room temperature, and allowed to stand for 3 hours. The precipitate was collected by filtration and recrystallized from a mixture of dimethylformamide and ethanol to give pale pink plates (3.1g.) of sodium 5-[2-[4-(2-oxo-5-chlorobenzothiazolin-3-ylacetyl)-1-piperazinyl]ethoxy]chromone-2-carboxylate.
m.p. 154° – 156° C (dec.).

Analysis for $C_{25}H_{21}N_3O_7SClNa \cdot C_2H_5OH$: Calculated: C 52.99, H 4.45, N 6.87, Na 3.76; Found: C 53.06, H 4.51, N 6.05, Na 4.03

EXAMPLE 8

2-(4-methyl-1-piperazinyl)carbonyl-5-(2-phenoxyethoxy)chromone

Thionyl chloride (35ml.) was added to 5-(2-phenoxyethoxy) chromone-2-carboxylic acid (2.6g.), and the mixture was refluxed under heating for 4 hours. The excess of thionyl chloride was removed first by distillation and then perfectly by washing several times with absolute benzene to give crude crystals of 5-(2-phenoxyethoxy)chromone-2-carboxylyl chloride. The crude product was dissolved in absolute benzene (ca.40ml.) and the solution was added dropwise with stirring to a solution of 1-methylpiperazine (1.6g.) in absolute benzene (50ml.) under ice cooling. The resultant mixture was stirred under ice cooling for 3 hours, and then allowed to stand overnight. The reaction mixture was poured in water. The aqueous mixture was alkalized with sodium bicarbonate and then extracted with ethyl acetate. The extract was washed with water and dried, and then the ethyl acetate was removed under reduced pressure to give a brown oil (0.9g.). The brown oil was separated and purified by column chromatography on alumina to give an orange oil (0.4g.). The pure oil was triturated from a mixture of benzene and ether to give pale yellow plates (0.35g.) of 2-(4-methyl-1-piperazinyl)carbonyl-5-(2-phenoxyethoxy)chromone.
m.p. 90° – 91.5° C.

Analysis for $C_{23}H_{24}N_2O_5$: Calculated: C 67.63, H 5.92, N 6.86; Found: C 67.80, H 5.97, N 6.69

EXAMPLE 9

2-(4-methyl-1-piperazinyl)carbonyl-5-(2-ethoxyethoxy)chromone 1-methylpiperazine (4.5g.) was added dropwise to a suspension of 5-(2-ethoxyethoxy)chromone-2-carboxylic acid (5.0g.) in chloroform (50ml.). A solution of phosphorus tribromide (2.0g.) in chloroform (10ml.) was added dropwise to the resultant mixture under ice cooling for 10 minutes. The mixture was stirred under ice cooling for 2 hours and at room temperature for additional 1 hour, and then ethyl acetate (250ml.) was added to the reaction mixture. The mixture was washed twice with 5% aqueous solution of sodium bicarbonate and with water in turn, and dried. The solvent was distilled off under reduced pressure to give 2-(4-methyl-1-piperazinyl)carbonyl-5-(2-ethoxyethoxy) chromone (500mg.). The product was derived in the usual manner to its maleate.
m.p. 69° – 71° C.

EXAMPLE 10

2-(N-hydroxycarbamoyl)-5-(2-phenoxyethoxy) chromone

To a solution of hydroxylamine hydrochloride (2.8g.) in methanol (15ml.) was added at 50° C an aqueous solution of potassium hydroxide (3.6g.) in methanol (10ml.) and water (2 drops). After the potassium chloride was precipitated under ice cooling, a solution of ethyl 5-(2-phenoxyethoxy)chromone-2-carboxylate (7.1g.) in methanol (50ml.) was added at a time to the mixture. The mixture was stirred at room temperature for 30 minutes, and filterd. The insoluble material was washed with hot methanol, and the washings and the filtrate obtained before were combined together and allowed to stand under cooling to give colorless needles. Th product was collected by filtration to give potassium salt (8.2g.) of 2-(N-hydroxycarbamoyl)-5-(2-phenoxyethoxy) chromone, suspended in water (100ml.) and acidified by adding acetic acid with stirring at room temperature. The mixture was shaked for 20 minutes, and the precipitated crystals were collected by filtration. The crystals were dissolved in dimethylformamide under heating and the insoluble material was removed by filtration. The filtrate was allowed to stand at room temperature. The precipitated crystals were collected by filtration, and recrystallized from a mixture of dimethylformamide and methanol to give white powder (3.2g.) of 2-(N-hydroxycarbamoyl)-5-(2-phenoxyethoxy)chromone.
m.p. 210° – 212° C. (dec.).

Analysis for $C_{18}H_{15}NO_6$: Calculated: C 63.34, H 4.43, N 4.10; Found: C 63.42, H 4.28, N 4.00

EXAMPLE 11

5-(2-phenoxyethoxy)chromone-2-carboxylic acid hydrazide

Ethyl 5-(2phenoxyethoxy)chromone-2-carboxylate (6g.) was dissolved in a mixture of absolute methanol (60ml.) and dry dimethylformamide (30ml.) under heating. To the resultant solution was added at a time a solution of hydrazine hydrate (1.2g.) in absolute ethanol, and the mixture was allowed to stand at room temperature for 3.5 hours. The precipitate was collected by filtration and recrystallized from a mixture of dimethylformamide and ethanol to give pale yellow, scaly crystals (3.2g.) of 5-(2-phenoxyethoxy)chromone-2-carboxylic acid hydrazide.
m.p. 200° – 201° C.

Analysis for $C_{18}H_{16}N_2O_5$: Calculated: C 63.52, H 4.74, N 8.23; Found: C 63.42, H 4.48, N 8.01

EXAMPLE 12

The following compounds were obtained according to a manner similar to that of Example 8.

(1) 2-(4-methyl-1-piperazinyl)carbonyl-5-(2-isopropoxyethoxy)chromone
(maleate) m.p. 80° C.

(2) 2-(4-methyl-1-piperazinyl)carbonyl-5-(2-propoxyethoxy) chromone
(maleate) m.p. 78° – 80° C.

(3) 2-[4-(2-hydroxyethyl)-1-piperazinyl]carbonyl-5-(2-phenoxyethoxy)chromone
(hydrochloride) m.p. 191° C.

What is claimed is:

1. A compound of the formula:

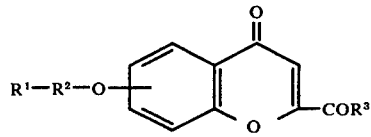

wherein $R^1$ is aryloxy substituted with lower alkylenedioxy, said aryloxy being phenoxy, napthyloxy, tolyloxy, xyloxy, mesityloxy or cumenyloxy;

$R^2$ is lower alkylene;

$R^3$ is hydroxy or lower alkoxy or a nontoxic, pharmaceutically acceptable salt thereof.

2. A compound of claim 1 in which $R^1$ is 3,4-methylenedioxy-phenoxy.

3. A compound of claim 1 in which said compound is sodium 5-[2-(3,4-methylenedioxyphenoxy)ethoxy]-chromone-2-carboxylate.

4. A compound of claim 1 in which said compound is ethyl 5-[2-(3,4-methylenedioxyphenoxy)ethoxy]chromone-2-carboxylate.

* * * * *